United States Patent [19]

Schwartz

[11] 3,941,565
[45] Mar. 2, 1976

[54] CLINICAL TESTING MEANS AND METHODS

[76] Inventor: Henry D. Schwartz, 111 Ashton Ave., San Francisco, Calif. 94112

[22] Filed: Jan. 2, 1973

[21] Appl. No.: 320,264

Related U.S. Application Data

[63] Continuation-in-part of Ser. No. 96,031, Dec. 8, 1970, abandoned.

[52] U.S. Cl. ............... 23/230 B; 23/253 R; 141/37; 204/1 T; 261/83
[51] Int. Cl.² ................ G01N 27/56; G01N 33/16
[58] Field of Search ...... 23/230 B, 253 R, 259, 292; 204/195 L, 195 M, 195 R; 261/82; 259/112, 113; 73/423 A; 141/37, 48, 64, 99

[56] References Cited
UNITED STATES PATENTS

| | | | |
|---|---|---|---|
| 651,727 | 6/1900 | Schneider | 141/37 |
| 3,206,172 | 9/1965 | Gaska et al. | 259/113 X |
| 3,467,582 | 9/1969 | Petersen et al. | 23/236 B X |

OTHER PUBLICATIONS

E. W. Moore, Chapter 7 of Ion-Selective Electrodes, Dept. of Commerce, Natl. Bur. Standards, Special Publication 314, 1969, pp. 215, 220, 221, 225, 226, 228, 229, 231, 233–236, 241, 243, 247 relied on.
Armour Pharmaceutical Pharmaceutical Co., Metrix Division, Normal Clinical Control Serum, May 1971, Lot. No 5431.
Armour Pharmaceutical Co., Metrix Division, Abnormal Clinical Control Serum, Mar. 1971, Lot No. 1015.
McLean et al., J. Biol. Chem. 108, 285–322 (1935).
Moody et al., Analyst, 95, 910–918 (1970), Nov.
Corning Scientific Instruments, Technical Information, Miniature Calcium Electrode, Catalog No. 476230.

*Primary Examiner*—Robert M. Reese
*Attorney, Agent, or Firm*—Wolf, Greenfield & Sacks

[57] ABSTRACT

Clinical testing means for determining pH dependent body fluid substances. In vivo ionized calcium concentration is obtained by withdrawing a blood specimen, determining the pH of the serum when withdrawn from the body and later, determining the in vivo ionized calcium concentration at the original pH. The pH of the serum is adjusted to the original pH by equilibration with carbon dioxide after which the ionized calcium concentration is directly electrically measured. Alternately, the original ionized calcium concentration is extrapolated or interpolated by making two different pH adjustments, electrically measuring calcium ion concentration, graphing the points obtained on semi-log paper to form a straight line graph from which the original calcium ion concentration can be obtained knowing the original serum pH. In still another variation, an extrapolation can be made to determine the carbon dioxide adjustment required to produce the original pH, after which pH adjustment the original concentration can be directly measured. Other variations of the methods are used to obtain less reliable but useful ionized calcium concentrations. A relationship between ionized calcium and total calcium in serum is used to determine total calcium levels. Multiple sample serum testing means has a rotatable sample container turntable and a cover means through which carbon dioxide can be simultaneously introduced into plural samples. The sampling means carries pH determining means and ionized calcium determining means for rapid ionized calcium measurements.

40 Claims, 13 Drawing Figures

INVENTOR
HENRY D. SCHWARTZ
BY
WOLF, GREENFIELD & SACKS

INVENTOR
HENRY D. SCHWARTZ
BY
WOLF, GREENFIELD & SACKS

CLINICAL TESTING MEANS AND METHODS

RELATED APPLICATION

This application is a continuation-in-part of applicant's copending application Ser. No. 96,031 now abandoned filed Dec. 8, 1970, entitled CLINICAL TESTING MEANS AND METHODS.

BACKGROUND OF THE INVENTION

For many years the medical profession has used clinical testing to determine total human serum calcium concentration in connection with diagnosis and treatment of various disease of the body including parathyroid disorders, tetany and bone structure diseases. Total calcium concentration of the serum includes both bound calcium and ionized or disassociated calcium. More recently, it has been recognized that the ionized calcium level is of significance in diagnosis and treatment of certain human malfunctions such as the diseases noted above. Knowing the total calcium concentration of a person, which can be measured by conventional means does not enable one to know the level of ionized calcium of that person. Thus, direct methods of measuring ionized calcium are desirable.

It has been difficult to clinically measure human serum ionized calcium concentrations of the body by conventional clinical laboratory procedures. However, one apparatus for directly determining ionized calcium concentration in protein-containing liquids such as blood serum has been developed and is the Orion Ionalyzer Serum Calcium Activity Flow-Through System such as model 99–20 (Orion Research, Inc., Cambridge, Mass. U.S.A.). This system, as is known, basically uses two or three aqueous standards of known ionized calcium concentration which are flowed in turn through a calcium electrode with the millivoltage produced being recorded. The millivoltage is plotted against the logarithm of the ionized calcium for each standard to produce a calibration graph. Blood serum sample millivoltage is then similarly measured and by means of the calibration graph its ionized calcium concentration extrapolated manually or automatically by an electrical calculator such as an Olivetti 101.

Thus, a method of directly measuring ionized calcium in a sample is available. However, certain problems arise in making useful and practical clinical determinations. When blood is withdrawn from its in vivo state in the body, its original pH in the body changes as time of exposure to air progresses. Thus, if ionized calcium is measured directly after withdrawal of the blood from a patient, reasonably accurate original or body serum ionized calcium concentration is obtained. However, such immediate measurement is often not practical because of distances between patients and the clinical laboratory as well as the volume of determinations to be made, shortages of personnel and the like.

The normal range of blood serum pH in humans is from about 7.27 to about 7.51 (at the 95% confidence limits) with a pH of 7.39 being considered an average, normal pH at normal body temperature of 37°C.

It has now been found extremely important for certain clinical testing purposes to know the pH of blood serum, i.e., blood, when in the body and correct for this pH in a blood sample in order to determine the actual ionized calcium concentration of the blood serum, i.e., blood, when the sample was in the body. It has not been recognized that it is important to adjust for and make an ionized calcium determination on the sample by artificially varying the pH of the sample whereby exact original pH of the sample is accounted for in measurement if extremely accurate measurement is desired. Moreover, it has not heretofore been known that there is a straight line relationship between pH and ionized calcium concentration of serum when plotted on semilog paper.

SUMMARY OF THE INVENTION

It is an object of this invention to provide practical methods for accurately determining ionized concentration of pH dependent substances such as ionized calcium concentration, in the body by clinical testing of a sample body fluid after the pH of the body fluid has changed from the pH present when the body fluid was in the body.

Still another object of this invention is to provide methods in accordance with the preceding object which are easy to carry out with minimized expense, yet, have high accuracy.

Still another object of this invention is to provide a method of determining total calcium originally in body fluid by means of ionized calcium measurements.

Still another object of this invention is to provide serum ionized calcium standards of accurate known ionized calcium content and unique methods of use.

Still another object of this invention is to provide screening methods for determining approximate original ionized calcium concentration in the body by clinically testing of a sample body fluid after it is withdrawn from the body.

Still another object of this invention is to provide novel and improved apparatus for use in clinically determining ionized calcium concentration of body fluids.

A still further object of this invention is to provide apparatus in accordance with the preceding object which can be rapidly and efficiently used with high accuracy.

According to the invention, original ionized calcium concentration of blood serum taken from the body is determined by testing to determine the original pH of the serum when it is removed from the body and later determining the ionized calcium concentration at the original pH. The original pH value can be determined by conventional means on the whole blood, or on the separated serum in contact with its clot, which values are the same. The ionized calcium concentration determination can be made with known equipment such as the Ionalyzer noted above.

When less accurate determinations such as screening tests are desired the original pH need not be measured and the methods of this invention are used based on the assumption that the serum tested had an original pH equal to the accepted average normal pH of about 7.39.

Preferably, the pH of the serum when ready for testing is adjusted to the original body pH of the serum by equilibration with carbon dioxide while simultaneously monitoring the pH of a serum sample to reach the original pH whereupon blending of carbon dioxide is stopped and a direct ionized calcium measurement is made. In an alternative form of the invention, the original ionized calcium concentration of the serum in the body is determined by establishing an arbitrary set value of carbon dioxide partial pressure in a serum sample and measuring a first ionized calcium concentration at the first pH value so obtained, then establishing a second arbitrary set value of carbon dioxide partial pressure in the sample and measuring a second ionized calcium concentration of the serum sample at the second pH value. The two arbitrary pH values are selected to be in the range of from pH 7.10 to pH 7.75. The first and second concentrations obtained are plotted on a semi-log paper graph with calcium ion concentration graphed against pH value to obtain two arbitrary points. The original body serum ionized calcium concentration is then determined by forming a straight line between the points obtained on the graph and reading the original ionized calcium concentration from the known original pH of the serum.

In still another alternate form of the invention, the original ionized calcium concentration is determined by determining the fresh or original pH value of the body fluid when it is withdrawn from the body, utilizing two arbitrary known carbon dioxide partial pressures by equilibration of the sample serum with carbon dioxide gas to produce two pH points in a serum sample. The logarithm of each carbon dioxide partial pressure is then plotted on semi-log paper, against the pH it produced to form two points which are connected by a straight line whereupon extrapolation can be used to determine the $CO_2$ partial pressure required to reproduce the original pH in the sample. The original pH is then reproduced by adjustment with the required carbon dioxide gas, and ionized calcium concentration corresponding to the original ionized calcium concentration of the sample is directly measured as by an Ionalyzer.

A method of determining ionized calcium concentration of serum taken from the body which is in some cases less precise and accurate, but highly useful as a screening procedure, comprises establishing a straight line graph on semi-log paper of pH plotted against ionized calcium of pooled normal serum with the line being determined by determining the pH and log ionized calcium of serum at at least two different pH values thereby defining a normal pH slope. The normal slope is then utilized to determine the ionized calcium concentration of any particular serum sample taken from the body. For example, the ionized calcium concentration and pH can be directly measured in a serum sample to be tested, this point plotted on semi-log line paper and a line of the normal slope drawn through this point so that a readout can be obtained on the last-mentioned line corresponding to an arbitrarily selected average normal pH of 7.39 or the actual pH of the serum when taken from the body if known. The pooled serum used is obtained from a large number of individuals such as for example at least 10 and preferably 100 humans so that an expected normal slope is obtained.

A method of determining original total calcium concentration in serum taken from the body after first determining ionized concentration of the serum is carried out by using the formula:

$$T_o = \frac{I_o V_a T_a}{I_f (V_o + V_a) - I_o V_o}$$

where all values except $T_o$ are obtained by the methods of this invention or by conventional measurement. This formula results from the finding of this invention that a ratio:

$$\frac{I_o}{T_o} = \frac{I_f}{T_f}$$

exists in any given serum between ionized calcium and total calcium which ratio can be solved for $T_o$ after obtaining $I_o$ and $I_f$ at the same pH value.

Preferred clinical testing apparatus for determining original ionized calcium concentration of a body fluid taken from the body is formed of an enclosed sample container for carrying a sample of the body fluid. The sample container is preferably interconnected with vibrating means for vibrating the sample in reciprocal straight line movement. The sample container defines a gas inlet means and first and second sampling tube means preferably arranged along axes corresponding with the straight line movement of the container.

A preferred testing apparatus for making multiple sample clinical determinations of original ionized calcium concentrations of body fluids taken from a body has a rotatable turntable in which are removably mounted a plurality of body fluid sample containers preferably having upwardly facing container mouths. A cover is positioned over the turntable to substantially close the container mouths while permitting rotational movement of the turntable with respect to the cover. Means are provided for rotating the turntable with respect to the cover at predetermined timed intervals to advance each of the containers to successive stations. Gas means preferably in the cover pass a gas to each of the containers at predetermined stations whereby the pH of serum samples carried by the containers can be adjusted. A sampling tube is mounted at one of the stations for withdrawing a sample serum portion from a serum sample container at that one station. Preferably the gas means is a continuous passageway having gas jet entrances corresponding to each station of the turntable.

It is a feature of this invention that original ionized calcium concentrations can be rapidly, accurately and efficiently determined. The term "original ionized calcium concentration" is defined as the ionized calcium concentration present in vivo in the body although the testing is carried out after withdrawal of the body fluid from the body. The turntable apparatus of this invention enables rapid testing of multiple samples since pH adjustments can be made simultaneously on many different samples prior to actual calcium ion testing as by an Ionalyzer at one position or station on the turntable. Only small modification of existing conventional equipment is necessary to carry out efficient testing of plural samples.

BRIEF DESCRIPTION OF THE DRAWINGS

The above and other features, objects and advantages of the present invention will be better understood from the following specification when read in conjunction with the accompanying drawings in which.

DESCRIPTION OF PREFERRED EMBODIMENTS

Figure 1:
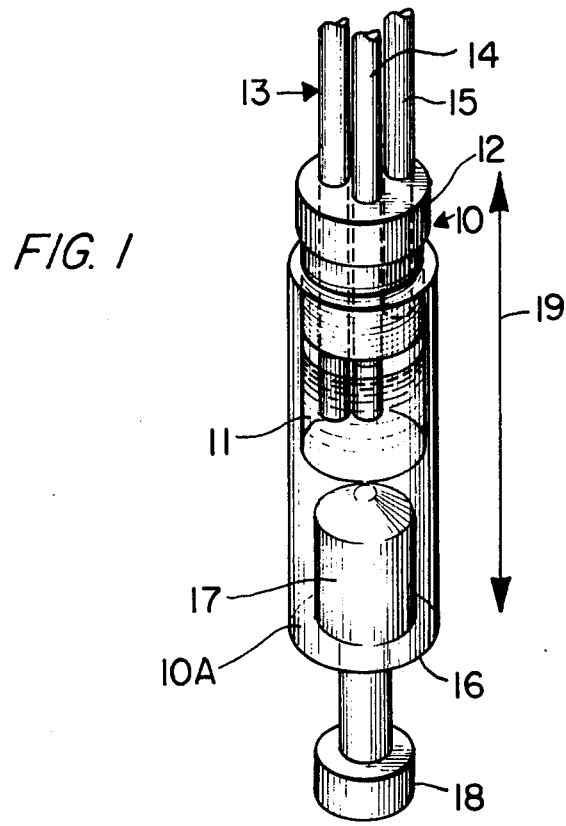
FIG. 1 is a side view of a preferred embodiment of a single sample apparatus of this invention.

According to the invention, the variation in pH of a serum sample from its original pH in the body, which occurs with time and exposure to air after withdrawal from the body, which variation is inversely proportional to ionized calcium in the serum sample, is taken into consideration when determining original in vivo ionized calcium concentration. Basically, the pH of a serum sample is determined before the serum sample has changed in pH from its original pH in the body. At a later point in time, where the pH has often varied, the ionized calcium concentration at the original pH is determined. This is accomplished by one of three basic alternative procedures.

In a first procedure, blood is withdrawn from the body and immediately tested to determine the pH before the pH of the sample withdrawn has changed from its in vivo pH. This is done using normal procedures such as withdrawal of blood and plasma under oil whereupon the pH is electrically tested usually within several minutes of withdrawal. The pH measurement can be made by any known apparatus but is preferably done with the use of a pH electrode as known in the art. This value is recorded. At a later point of time, when convenient, actual testing of the ionized calcium of the sample is carried out. The testing is carried out by flowing carbon dioxide gas over the sample, admixed with a gas nonreactive with the sample such as air, while monitoring the pH of the sample until the original pH as previously determined is reached. The mixture of air and $CO_2$ is monitored by the test operator as required to reach the original pH. At that point, ionized calcium concentration of the sample is measured preferably electrically with a calcium electrode electrical test device such as an Orion Ionalyzer to give a direct reading of ionized calcium corresponding to the ionized calcium concentration in the body at the time the sample was withdrawn from the body.

In a second procedure, a blood sample is withdrawn and the original pH tested and recorded as described above. Carbon dioxide gas preferably admixed with air at two arbitrary carbon dioxide concentrations are then used in turn to produce two different pH's in the sample serum within the range of pH 7.10 to 7.75. This is done by adding, for example, 2.5% or 20.0 mm Hg pressure carbon dioxide in an air mixture to a sample and simultaneously measuring the pH and the ionized calcium at that first aribtrary pH value produced in the sample. The step is then repeated using 7.5% or 60.0 mm pressure carbon dioxide in air mixture and again measuring ionized calcium at the second arbitrary pH value which is also measured. The ionized calcium concentration obtained at the two pH values are then graphed on semi-log paper as for example shown in FIG. 6 where ionized calcium concentration is plotted against pH to determine points A and B. A straight line is drawn between the points and knowning the original pH, the original ionized calcium concentration of the sample when in the body can be extrapolated easily as at point C. It is important to use conventional semi-log paper since it has been found that there is a straight line relationship between serum pH and ionized calcium concentration when so graphed at least in the range pH 7.10 to pH 7.75.

Figure 7:
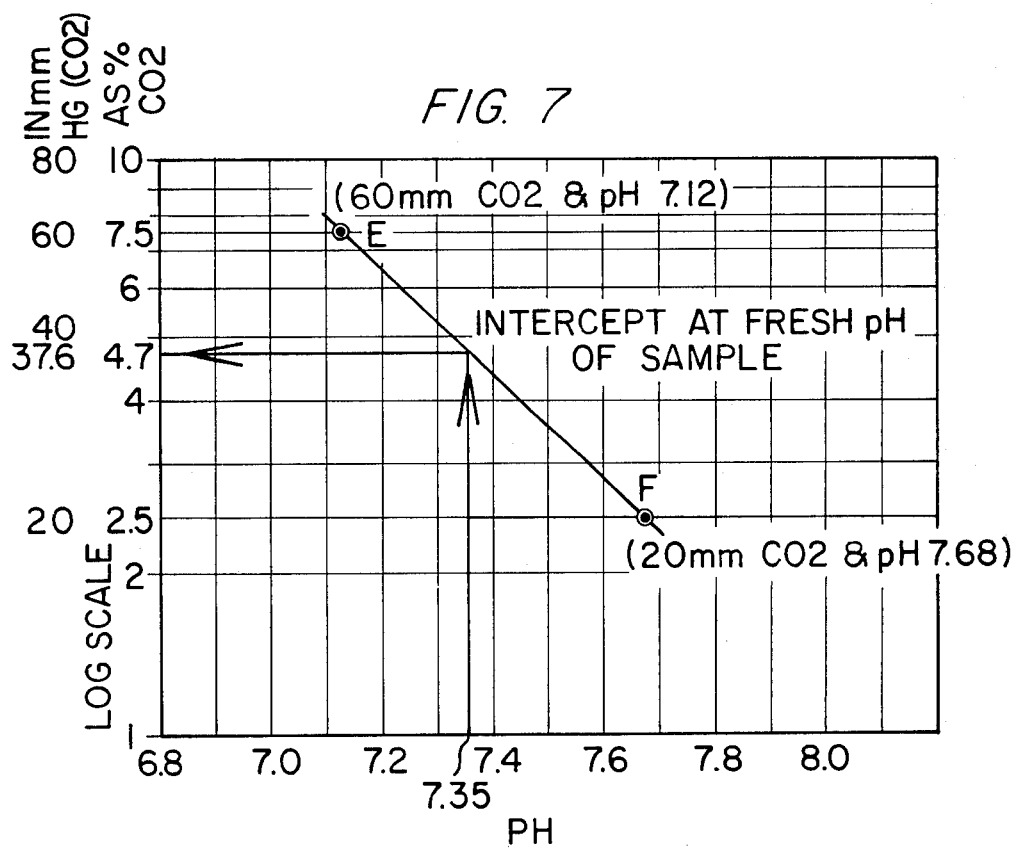
FIG. 7 is a graphic illustration of an alternate embodiment thereof.

In a third procedure, the serum sample is obtained as previously described and the original pH determined as previously described. When the sample is ready for testing, it is treated with a known, arbitrary carbon dioxide partial pressure and the pH produced is measured. The serum sample is then again treated with another known, arbitrary carbon dioxide partial pressure and the pH is again measured as illustrated in FIG. 7 to obtain points E and F. The points are graphed on semi-log paper as shown in FIG. 7 and a straight line used to interconnect the points. This is the same procedure used in standard Astrup blood gas determinations. Using the original pH value of the serum sample, the carbon dioxide concentration corresponding to that present in the original sample when in the body can be determined. The serum sample is then adjusted in its carbon dioxide concentration or partial pressure to that of its original carbon dioxide concentration at which point ionized calcium can be directly measured in the serum sample and the concentration obtained corresponds exactly to the original ionized calcium concentration in the body.

In all cases, it is preferred to maintain temperature of all pH and ionized calcium concentration determinations at a constant value during each of the actual testing steps such as pH readings and ionized calcium concentration readings. This is preferred since there is some slight variation with temperature differences. Temperatures in the range of from 22°C to 38°C are preferably used. The tests and procedures given in this application have been carried out at room temperature (27°C) for convenience as is customary. However, other temperatures can be used. All average normal values and other values, except pH values are given in this application at a temperature of 27°C. For purposes of convention, all pH values are given at their equivalent values at 37°C. Extremely small serum samples can be used such as for example serum samples of from 1 to 3 ml using conventional pH and ionized calcium test devices.

Turning now to apparatus useful in carrying out the invention, a sample holder container is illustrated at 10 and comprises a clear plastic body 11, of cylindrical shape which defines an internal chamber preferably of small size sufficient to carry for example a 2 ml sample of serum to be tested. At its upper end a snap-on cap 12 encloses a mouth of the body and carries passageways therethrough for snug sliding fit of a sampling tube 13 for sampling the serum to determine ionized calcium concentration of the serum sample as by withdrawing a portion through the tube, a pH electrode 14 which is introduced below the level of the serum and a gas flow tube 15 for introducing carbon dioxide gas preferably admixed with air to adjust the pH of the serum sample as required.

Preferably the container 10 is held in snug fit in a cylindrical recess of a container holder 10A which has an upwardly extending cylindrical boss 17 sized to snugly fit the operating end of a linear vibrator 18. It should be noted that the passageways for tubes 13, 14 and 15 have axes parallel to the line of motion 19 of the linear actuator. This is done so that stiff rigid tubes 13, 14 and 15 can be used if desired with the tubes reciprocally sliding with respect to the sample cup during vibration. Moreover, the sliding fit enables gas flow in the container 10 since gas passed over the sample from the tube 15 escapes through the space between the tubes 13 and 14 and the cap.

The linear vibrator 18 can be any standard linear vibrator to assure thorough mixing of the carbon dioxide gas with the sample. Fisher scientific model 1-914-25V1 is particularly useful. The particular pH electrode and associated apparatus for readout can be any of the known continuous reading pH devices. A known I. L. Deltamatic pH meter model 245 having a continuous pH readout is particularly useful. The pH electrode used preferably has a diameter of less than 8 mm, and can be the I. L. pH electrode Model 14153. Tube 13 is preferably connected with a calcium activity flow-through system which utilizes a calcium electrode and electrically measures calcium ion concentration in millivolts. Orion Ionalyzer Serum Calcium Activity Flow-Through System model 99–20 and its associated millivolt readout of an Orion model 801 digital pH/mV meter is preferably used for interconnection with the sampling tube and in association with the pH electrode and pH meter. Dip calcium electrodes of known design can also be used and enable a reading to be obtained merely by dipping the electrode in a sample rather than flowing the sample through the electrode. Dip electrodes are preferably used where a single sample is changed rapidly in pH value since such electrodes are better able to give a continuous readout rapidly responsive to sample changes.

In using the container 10, after adjustment of the sample pH by flow of carbon dioxide gas over the sample serum, while monitoring the pH, to obtain the desired pH of the sample, a small amount of the serum in the serum container 10 is drawn up through the tube 13 and passed to the calcium electrode to obtain the millivolt readout corresponding to a known ionized calcium concentration. As known in the art, the calcium electrode can be standardized with standardized calcium concentration solutions to enable millivolt readout to be directly translated into ionized calcium concentration.

While single sample ionized calcium sample concentration testing as described with regard to the apparatus of FIG. 1 is useful, it normally is time consuming. Average serum samples which have been exposed to air for several hours may have pH's that have risen to 7.9 or thereabouts and it normally takes about 10 minutes to add sufficient carbon dioxide to bring the pH down to approximately the "normal" range of from pH 7.27 to 7.51 after which additional carbon dioxide can be added to obtain the exact pH. If a plurality of samples are handled together, considerable time can be saved by exposing many samples to a predetermined carbon dioxide concentration to roughly bring the samples to the pH normal range where it is preferred to test them for ionized calcium concentration. Thus, a plurality of samples are treated during one time interval after which each is ready for rapid readjustment and/or testing since only small variation in carbon dioxide need be used to obtain the desired pH. A preferred apparatus and system for carrying out plural sample testing in accordance with this invention is semidiagrammatically illustrated in FIG. 2 at 20.

Figure 2:
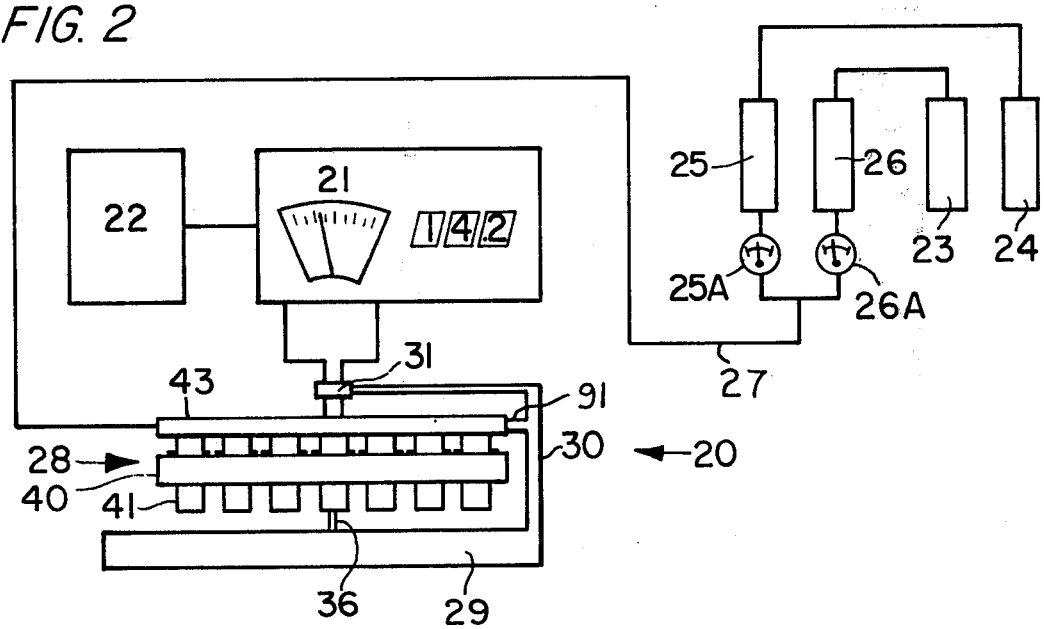
FIG. 2 is a semidiagrammatic showing of an alternate apparatus of this invention.
Figure 3:
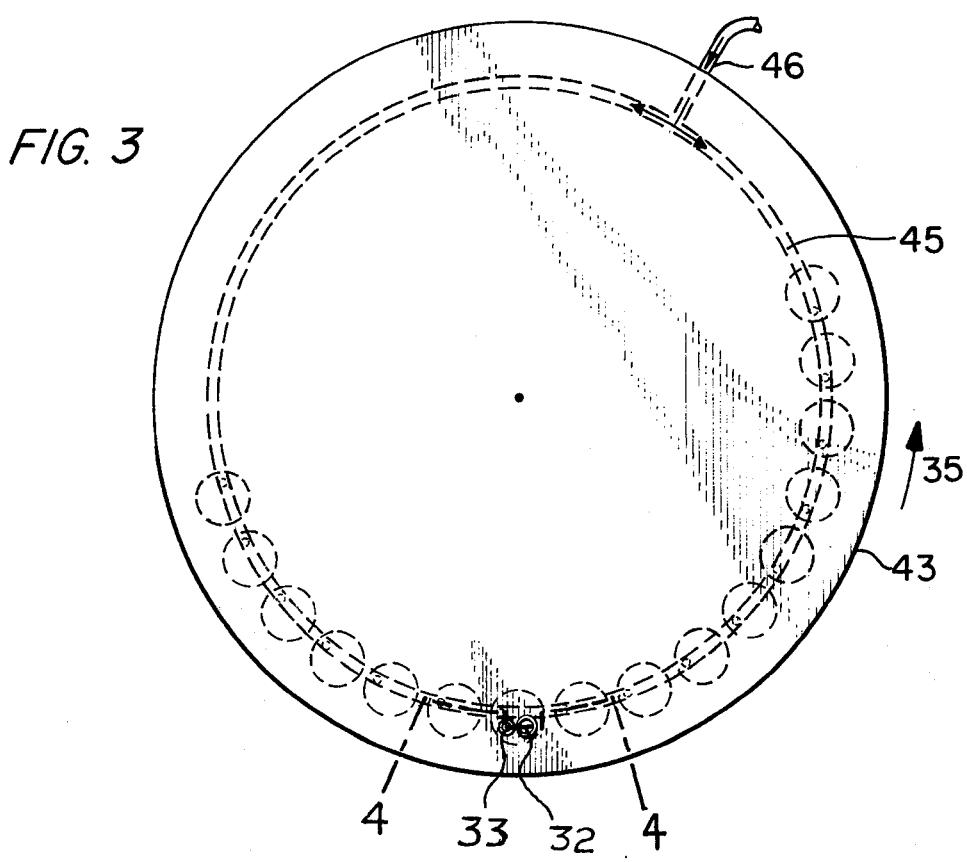
FIG. 3 is a top plan view of an element thereof.
Figure 4:
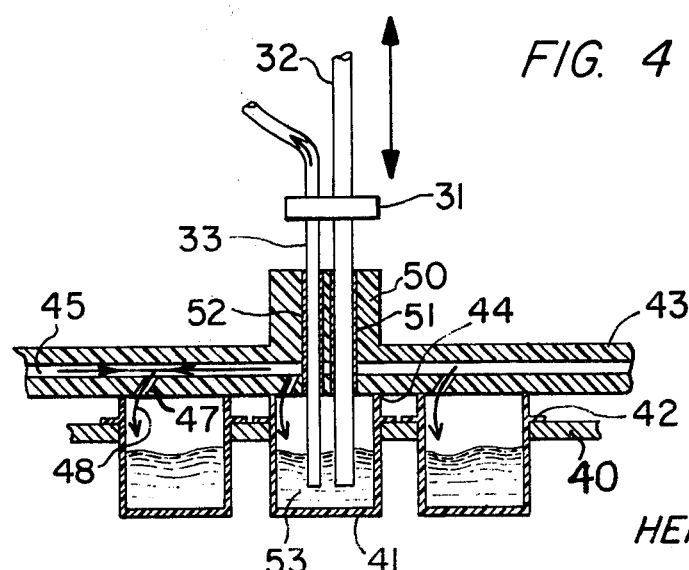
FIG. 4 is a fragmentary cross sectional view taken through line 4—4 of FIG. 3.
Figure 5:
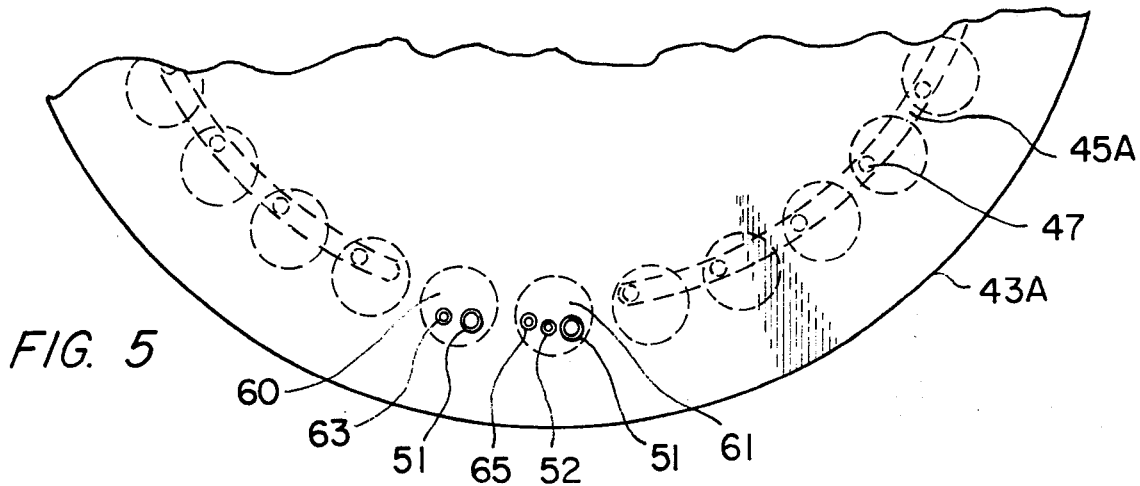
FIG. 5 is a top plan view similar to FIG. 3 but showing another embodiment thereof.

The system 20 has an ionized calcium concentration electrical test device such as the Orion Ionalyzer 21 as previously described and associated pH meter which may have a calculator 22 attached thereto, carbon dioxide and air sources 23 and 24 are interconnected by conduits to wash tanks 25 and 26 which are in turn interconnected to a common conduit 27 for blending through individual pressure gauges and on-off valves 25A and 26A. The square 21 represents the pH meter and digital pH/mV meter previously described. The electrode of the pH meter, the sampling tube of the Ionalyzer and the gas conduit 27 are connected with a turntable device 28 as best illustrated in FIGS. 2–4.

The turntable device 28 is the heart of the multi-sample system and permits rapid testing of plural samples.

The device is preferably a modification of existing laboratory equipment known in the art. A conventional Technion autoanalyzer model Sample 4 forms the major portion of the turntable device 28. As known in the art, the autoanalyzer comprises a base 29, a support 30 for a reciprocally vertically moving sampler block 31 which provides for linear movement of a pH electrode 32 and a stiff sampling tube 33 as will be described. A conventional, circular, horizontally mounted turntable 40 is mounted for rotation in the direction of arrow 35 on a central spindle 36. The turntable 40 carries preferably identical 2 ml or 4 ml sample cups or containers 41. Any number of sample containers 41 can be provided although in the preferred embodiment, thirty cups are uniformly arranged about the periphery of the turntable. The sample containers 41 as known in the art for use in the autoanalyzer each have an outwardly extending continuous flange 42 which enables them to pass through a hole in the turntable and be suspended therein.

A stationary cover disc 43 is positioned substantially parallel to the top of the turntable 40 so that the mouth 44 of each sample container is substantially closed to the atmosphere and in sliding contact with the bottom surface of the cover 43. However, the sliding and abutment of the mouth with the bottom surface of the cover 43 allows some gas flow to the atmosphere when gas is passed into the containers. This escape of gas permits entry of $CO_2$ gas and mixing of the gas with the liquid due to the jet mixing action of the gas. Preferably the cover fits around the spindle 36 at its center and is retained in a stationary position by an extension 91 to member 30 as known with conventional autoanalyzers. Thus, the weight of the cover causes the cover to seal the container mouths; however, a slight rise in gas pressure in the container permits gas flow between the cover and the container mouths. In some cases, a tight gas seal between the container mouth and the cover can be formed as by using an O-ring or a polytetrafluoroethylene collar mounted on the container top. This permits a sliding yet gas-sealed movement of the containers with respect to the cover. Thus, when a gas seal is used on selected containers, no gas entry or pH adjustment occurs in the selected containers. If all the containers are fitted with gas sealing means, gas entry and mixing can be allowed in selected containers by providing such containers with a gas outlet carried in the collar or cup body above the level of the liquid and in the form of a hole or slit or by an outlet in the cover.

As best shown in FIGS. 3 and 4, the cover 43 is of a thin plastic such as a ¼ inch thick Lucite and has a circular continuous conduit 45 with a common manifold 46 for interconnection with conduit 27. Gas conduit 45 has a plurality of angled outlets 47 preferably at 45° each forming a station of locus for gas treatment of the sample containers on the turntable. As best seen in FIG. 4, the outlets 47 are angled to allow gas to follow the path of arrow 48 and thus create a swirling action with serum contained in the serum sample containers enabling rapid mixing. In some cases, the gas can be pulsed in the conduit 45 to add to the mixing action caused by gas entry to the containers.

As known in the art, the turntable rotates intermittently in the direction of arrow 36 so that each sample container is presented at each station defined by an outlet 47 for a predetermined period of time when motion of the turntable stops after which rotation begins and stops again in predetermined sequence. Thus, when a carbon dioxide-air mixture is fed into the gas conduit 46, all of the sample containers will be simultaneously treated with the carbon dioxide mixture allowing sufficient time for a desired carbon dioxide partial pressure in each sample to be reached. One station directly below the vertically moving support head 31 is adapted for actual sampling of the serum and pH electrode testing. As best seen in FIG. 4 at the station shown in the center, two Teflon tubes are vertically arranged and passed through an enlarged boss portion 50 of the cover disc 43 and are noted at 51 and 52. The vertically movable support 32 carrying the pH electrode and sampler tube 33, which are themselves preferably coated with a thin Teflon coating, is designed to rasie the pH electrode and sampler tube by sliding the tubes 51 and 52 to a point above the lowermost surface of the cover 43 when the turntable rotates and to automatically lower the pH electrode and sampler tube when the turntable is stationary, thus permitting contact with a serum sample 53 in each serum sample container 41 as it passes the testing station. It is important that vertical movement be used so that a tight slip fit can be maintained between the tubes 51 and 52 and the electrode 32 and sampler tube 33 respectively enabling reciprocal up and down movement when required while retaining substantial gas sealing properties.

If desired, a vibratory device such as a linear vibrator can be interconnected with the base of the autoanalyzer or the central spindle to provide linear vibration. It should be noted that linear vibration allows sliding of the sampling tube 33 and electrode 31 without damage thereto and with sealing properties retained. Such vibration is not ordinarily necessary when swirling action is obtained by the angled jet outlets 47 since thorough mixing is easily accomplished.

In a modification of the turntable device 28, the upper disc cover 43 is modified as shown in 43A so that the gas conduit 45A is discontinuous leaving a final adjustment station 60 and a measuring or testing station 61 which are not interconnected with the conduit. This cover modification is employed where the test procedure used differs slightly from the test procedure that would be used with cover 43 as will be described. In this embodiment of the cover station 60 defines a Teflon tube 51 for mounting of a pH electrode 32 on the support 31 and a direct through hole for a stationary carbon dioxide gas tube 63 passing to the lower face of the cover. Station 61 carries tube 51 and 52 as previously described and is identical to the testing station shown in FIG. 4 with the addition of an independent stationary fixed gas tube 65 which passes directly through the cover to the lower surface of the cover 43A for exposure of gas to the sample at the measuring station.

It should be noted that the gas conduit 45A allows for simultaneous adjustment of pH in a plurality of samples and maintaining of the pH even during testing of individual ones of the samples while making final pH adjustments at the final adjustment station and ionized calcium determinations at the measuring station.

Examples of the three basic procedures utilizing various ones of the apparatus disclosed are given below. In each case, a sample of blood is drawn on the patient in a conventional manner as with the use of a syringe. A portion of the blood is preferably placed in a test tube at 27°C and clot formation occurs in several minutes whereupon the serum is separated and will be referred to as "Jones' serum" hereafter. Another portion of the blood is placed under oil or heparin in a conventional manner and an immediate pH measurement is made on the whole of the blood of the second portion using a conventional pH electrode which indicates a pH of 7.35 which is the original pH of the serum when in vivo. As a control merely to illustrate the invention, the serum sample prior to any pH change after removal from the body, is tested with the Ionalyzer after the Ionalyzer has been calibrated and the ionized calcium concentration is found to be 3.80 mg% which is the in vivo ionized calcium concentration. The Jones serum sample after separation from the clot, can be refrigerated if desired or can remain at room temperature for long periods of time up to thirty-six hours or more. This Jones serum is then used in the following examples:

EXAMPLE 1

The single sample vibrating apparatus 10 is used and is interconnected with the pH electrode 14, Ionalyzer sampling tube 13 and carbon dioxide-air source through tube 15 interconnected with tube 27 of FIG. 2. 2 ml of Jones' sample serum which has been standing in a standard 4 ml polystyrene cup at 27°C open to the air for 3 hours after withdrawal from the patient is placed in the cylindrical recess of the container holder 10A and the cover 12 is then put on it. A pH is measured indicating 7.80. Gentle vibration of the serum sample is started by activation of the vibrator 18. Suitable hand control valves are provided on the carbon dioxide and air suply tanks to enable variation in the partial pressure of the gas entering through tube 15. The continuous pH electrode operates and the operator views the readout of the pH electrode adjusting by hand the carbon dioxide and air mixture. Thus, the operator need not know the exact mixture since continuous pH reading is obtained and visually present enabling adjustment as needed. If for example the partial pressure of the $CO_2$ entering the sample container for about 8 minutes 40 millimeters, we find the pH after 8 minutes is about 7.30. Since the operator knows that he wishes to reach a pH of 7.35, the air tank valve or the $CO_2$ valve is adjusted accordingly to decrease the proportion of $CO_2$ a little until the pH meter reads 7.35, the original pH. The sample tube is activated to withdraw a sample of the serum which passes to the calcium electrode of the Ionalyzer and a millivolt readout displayed which millivolt readout is recorded. The millivolt readout is of course directly translatable into the ionized calcium concentration of the sample at pH 7.35 which concentration is 3.80 milligrams %. The calcium electrode actually measures calcium activity which is accepted as ionized calcium concentration. This corresponds to the fresh or original ionized calcium concentration as measured before as a control.

EXAMPLE 2

Figure 6:
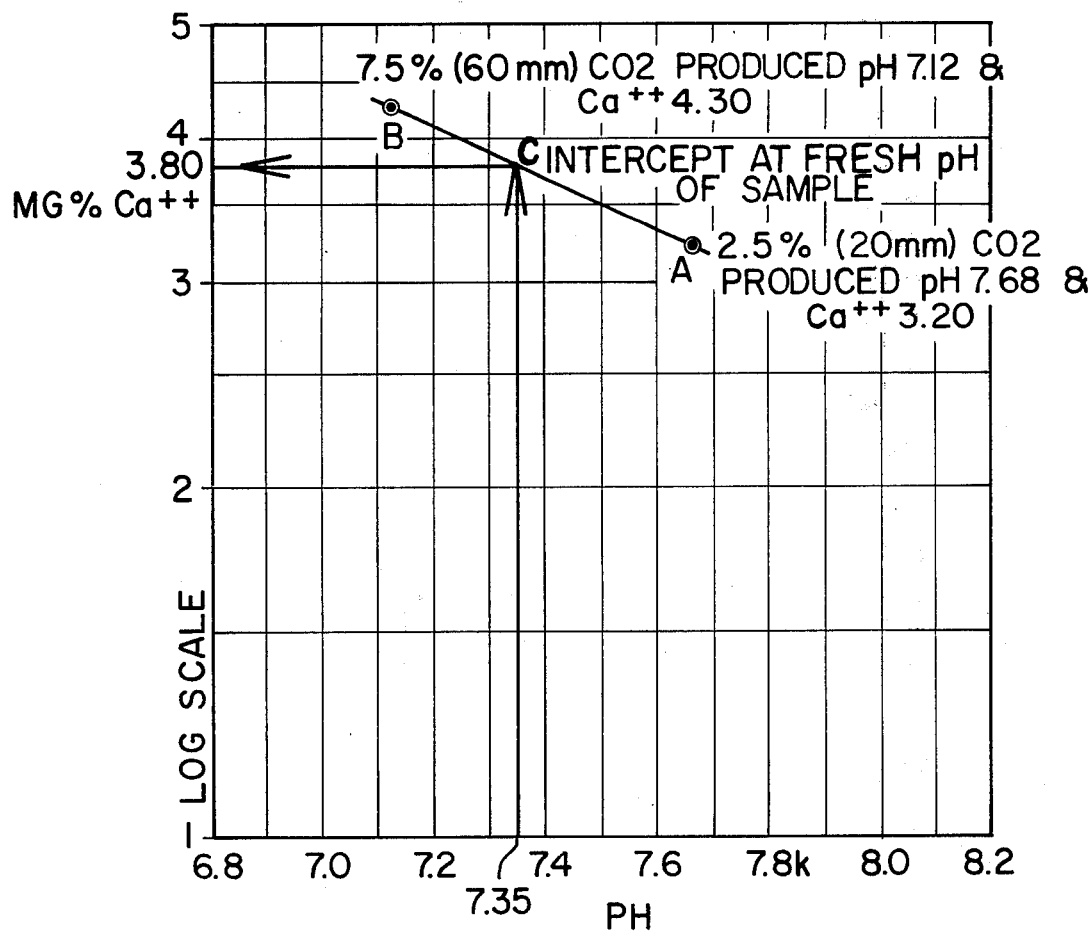
FIG. 6 is a graphic illustration of a preferred embodiment of this invention.

In this example, the container 10 is used along with an extrapolation procedure. 2 ml Jones serum sample as described in Example 1, is placed in the container body 11. A carbon dioxide-gas mixture at an arbitrary carbon dioxide partial pressure of 20 millimeters mercury is passed into the sample container through tube 15. After several minutes, the sample pH is found to be 7.68 at which point, 0.15 ml of the sample is directed through the calcium electrode and the ionized calcium concentration directly measured and found to be 3.20 mg%. The arbitrary point A is then plotted on semi-log paper as shown in FIG. 6. The partial pressure of the carbon dioxide is then changed to 60 mm and the process repeated to obtain point B. A straight line is then drawn between them. Extrapolation from the graph shows that at the known original pH of 7.35, the ionized calcium concentration of the sample is 3.80 mg% which is the correct original ionized calcium concentration of the serum in the body as known from the control value previously obtained.

EXAMPLE 3

The sample container system 10 is again used along with the carbon dioxide extrapolation technique method utilizing Astrup nomograms. Astrup nomograms make use of the fact that at a plot of log $pCO_2$ VSpH a straight line is obtained. 2 ml of the Jones serum sample used as in Examples 1 and 2 is placed in the container body 11 which is closed with cover 12 and placed in the holder 10A. The gas tube carries a known carbon dioxide-air mixture having a carbon dioxide partial pressure of 20 mm which is again an arbitrary value. After several minutes of exposure to this atmosphere and equilibration of the partial pressure of $CO_2$ in the sample, the continuously reading pH meter shows a pH of 7.68. This value is plotted on the graph as shown at F in FIG. 7. An arbitrary value of 60 mm partial pressure carbon dioxide is then used for a period of several minutes and the pH is found to be 7.12 which is plotted as point E on the semi-log graph. A straight line is formed between the two and it is extrapolated from the graph that at the known original pH of 7.35 a carbon dioxide concentration of 37.6 mm was present in the serum. The operator then adjusts the gas partial pressure by manipulation of valves on the carbon dioxide and/or air supply to obtain a partial pressure of 37.6 mm of carbon dioxide in the serum and a pH of 7.35 in the sample. The sampling tube 13 is then used to sample the serum with the Ionalyzer showing the ionized calcium concentration to be 3.80 mg% which indicates the original concentration and can be checked by the control used. Of course it should be understood that the control is used in these Examples only to illustrate the invention and the control measurement would not ordinarily be made because of inconvenience and other problems as discussed above.

EXAMPLE 4

The system of FIG. 2 with the cover disc 43 is used in the extrapolation procedure illustrated by FIG. 6. Jones' sample serum as used in Example 1 is used as one of the serum samples in a container 41. 2 ml of the sample is used in the container. Twenty-nine other test samples from twentynine other test patients are similarly prepared and 2 ml serum quantities are placed in each of the sample containers. The samples can be placed in the turntable by removal of the cover which is preferably removably fixed in place during operation of the turntable. A carbon dioxide-air mixture of approximately 20 mm partial pressure carbon dioxide, which need not be known or recorded, is circulated in the circular ring gas conduit 45 and intermittent rotation of turntable 40 started.

The cycle time is alternate rotation and stationary action at each 60 second interval. After about 10 minutes of gas flow, when the Jones serum sample as used in Example 1 is stationary at the measuring station below the support 31, with the pH electrode 32 and sampling tube 33 in the serum, the cycling and measuring is activated, the pH meter reading of the sample serum is recorded and a sample portion of the serum is drawn into the tube 33 for delivery to the calcium electrode to enable a simultaneous ionized calcium reading to be obtained and recorded. These operations are preferably carried out automatically although they can be done by an operator manually. When done automatically, the information can be printed out by a digital printer or stored in a conventional computer memory. The pH measured is found to be 7.68 and the ionized calcium at this pH is 3.20 mg%. The turntable 40 continues cycling and the process continues until all thirty samples are measured with simultaneous pH and ionized calcium concentration of each recorded at which point Jones' sample serum is back at the measuring station again. An arbitrary different $CO_2$-gas mixture having for example 60 mm $CO_2$ partial pressure is then circulated in the conduit 45 for about 10 minutes. The pH electrode and sampling tube are again activated with the simultaneous values of each sample tested and recorded. Jones' sample is found to have a pH of 7.12 and ionized calcium of 4.30 mg%. The 2 points obtained for each sample are then plotted on semi-log paper as shown in FIG. 6 in the plot for the Jones sample. Knowing Jones' fresh or original serum pH of 7.35, extrapolation to the ionized calcium corresponding to this shows the original ionized calcium concentration of the serum to be 3.80 mg%. Of course similar graphing and calculation is made for the other samples. In this case, 2 determinations of ionized calcium are made on each sample requiring twice as much serum for testing. The time period of testing can be extremely rapid with about 10 minutes for each of the two exposures and equilibrations to the two different partial pressures and 1 minute for measuring each sample repeated twice for a total of 1 hour and 20 minutes for the thirty samples.

It should be noted that conventional equipment as previously described can be used to actuate all necessary movements and measurements as well as record, plot and extrapolate final values desired.

EXAMPLE 5

The system of FIG. 2 is used with the cover 43A and a procedure in which each serum sample is brought to the original pH of that serum prior to ionized calcium testing. Samples are selected as in accordance with Example 4 and all serum samples are subjected to a $CO_2$-air mixture with $CO_2$ of 40 mm partial pressure for about 10 minutes to preferably bring all of the serums within a normal pH range. The turntable 40 is then actuated with the Jones serum used in Example 1 at the station immediately prior to the final adjustment station 60. The turntable 40 then rotates and stops with the test serum at the final adjustment station 60. The pH electrode 32 and sampling tube 33 are at the measuring station 61 in their lowermost position and an identical pH electrode 32 is at the final adjustment station 60 in its lowermost position. The pH electrode at the final adjustment station shows a reading of pH 7.30. Since this final adjustment station has an independent gas entry tube 63 interconnected with carbon dioxide and air tanks with suitable valving as does the measuring station 61, it is possible to manually adjust the $CO_2$ and air proportions to produce the original pH of 7.35 as measured at station 60 just as is done in Example 1. The difference is that the gross pH adjustment with 40 mm partial pressure $CO_2$ has already been done on all of the samples so that only small adjustments would normally have to be made at the final adjustment station. After approximately 1 minute in the stationary position when the desired pH has been reached the sample containers then advance 1 position bringing the Jones test serum into the measuring station position 61. The same gas combination which was used in the final blending of the Jones serum in the final adjustment station is then directed into the Jones serum in the measuring station. This can be done by manual adjustment or automatically by the use of flow meter controls automatically adjusted in accordance with flow meter controls for the gas flow in the final adjustment station. In the calcium measuring station 61, the pH electrode records the same pH as 7.35 and the sampling tube simultaneously withdraws a sample to the calcium electrode which measures 3.80 mg% of ionized calcium. All 30 samples rotate and are measured. This procedure enables use of only 1 calcium measurement requiring smaller amounts of sample serum than in Example 4. The total time required is 10 minutes for initial adjustment or equilibration of $CO_2$ partial pressure plus 1 minute per sample, a total of 40 minutes to completely process and test thirty samples. It should be understood that while a sample is at the calcium measurement station having its ionized calcium recorded and pH recorded (the latter merely to confirm the pH is the same as it was brought to in the previous final adjustment station) the next sample is getting a simultaneous final treatment to adjust to the original pH of that next sample. In some case, the pH electrode 32 at the measuring station 61 can be eliminated since it is merely used to confirm the reading at the final adjustment station 60. Elimination of the electrode at station 61 permits use of only 1 pH meter and readout rather than 2 meters necessary when 2 pH electrodes are used.

EXAMPLE 6

The apparatus and system of Example 5 is used, with a $CO_2$ extrapolation procedure. Jones' sample is identical to the Jones' sample used in Example 5. All of the samples used are mixed with $CO_2$ gas mixed with air at a $CO_2$ partial pressure which must be precisely known and can be obtained from suitable flow-meter gauges such as 25A and 26A. An arbitrary known $CO_2$ partial pressure of 20 mm $CO_2$ partial pressure is used in the gas conduit 45A. The independent gas entry tubes in the final adjustment and calcium measuring stations 60 and 61 are both set to the same $CO_2$ partial pressure as used in the circulating ring 45A. After 10 minutes the turntable begins its rotational cycle and the pH of Jones' sample serum as used in Example 1 is recorded at the calcium measuring station 61. The Jones serum ph is found to be 7.68. After all samples have been thus measured, another known arbitrary $CO_2$ partial pressure of for example 60 mm is then circulated in the gas tube 45A and measurement of the pH of the serum after a 10-minute interval is found to be 7.12. As shown in FIG. 7, these values are plotted on semi-log graph paper whereupon extrapolation from the fresh pH of 7.35 is made finding that 37.6 mm $CO_2$ would produce in the original test serum the required pH of 7.35. The required pH for all of the samples is similarly calculated in turn. All of the samples then begin their rotation to pass for a third time through the measuring and final adjustment stations. The samples are then treated as in Example 5 except that instead of having to manually adjust valves to obtain the correct $CO_2$-air mixture in response to the pH reading, one knows in advance the exact $CO_2$ partial pressure required to produce the required pH and suitable settings can be made on the gas controls. One can blend gases to equilibrate the serum to 37.5 mm partial pressure of $CO_2$ which one determines from graph of FIG. 7 to be needed for Jones' serum and a pH of 7.35 is automatically produced at the final adjustment station and confirmed by the pH reading. The 37.5 mm of $CO_2$ partial pressure is used in Jones' serum at both the final adjustment station and the measuring station while the sample tube withdraws a portion of the sample and measures the ionized calcium which is 3.80 mg% as expected.

Figure 8:
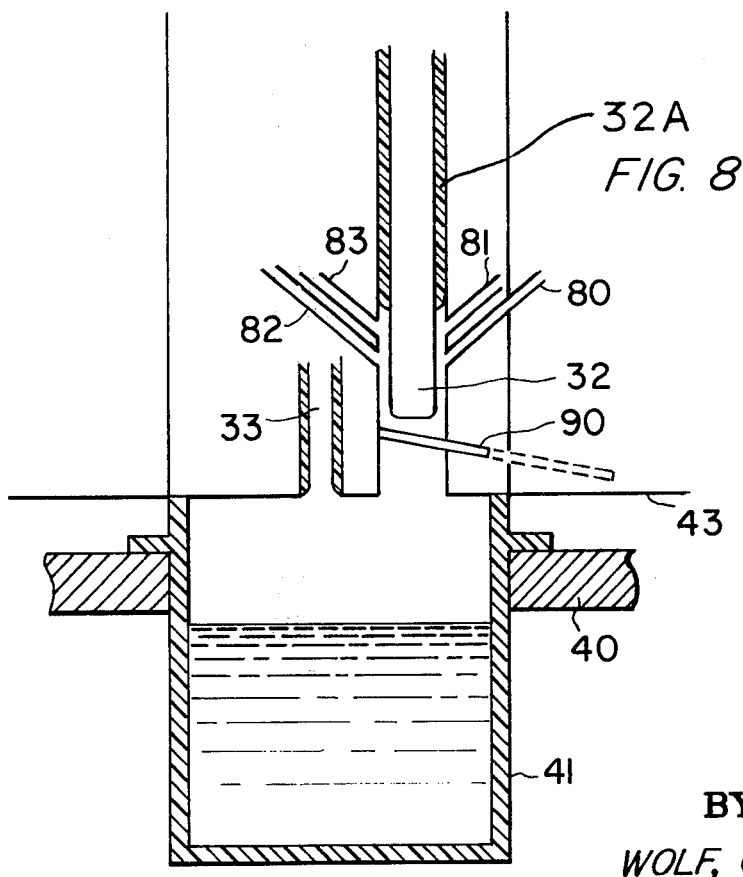
FIG. 8 is a diagrammatic side view of an accessory structure useful in the apparatus of FIGS. 3 and 5.

While specific embodiments of the method and apparatus of this invention have been shown and described, many variations are possible. For example, FIG. 8 diagrammatically illustrates a means and method for cleaning the pH electrode after each cycle of the electrode. The electrode 32 with its Teflon coat 32A is shown in its uppermost position with its end within the raised block 50 of the cover 43. A sliding member 90 seals the bottom of the passageway of the electrode when the electrode is in its raised position and passageways 80 and 82 can be used to flow water about the tip of the electrode 32 after which air is passed through conduits 81 and 83 to blow out a portion of the water and dry the electrode. Any water remaining can be removed by the air blast or can be carried in a groove in the sliding member 90 when it opens just prior to positioning of a cup 41 under the electrode and prior to downward movement of the electrode. Other alternate procedures for cleaning the electrode between samples can be used if required for more precise pH measurements than obtained without a cleaning step.

When the standard Orion Ionalyzer is used, the sampling tube is used in conjunction with a small pump which pumps the serum up into the calcium electrode thereof.

While the plural sample means and method have been described without specific examples showing standardization, such standardization can be carried out by conventional methods. Calcium solution standards can be used in place of some of the samples in the turntable used if desired. If the voltage drift in a particular laboratory is high, a Ca++ standard can be interposed however frequently such standard is required to produce the desired precision once the device is calibrated. It is preferred to use calcium standards in body serum rather than aqueous standards as will be later described herein.

$CO_2$-air mixtures have been described. However, the $CO_2$ content of the serum samples can be adjusted by admixing $CO_2$ with other gases than air which do not deteriorate the serum or affect the pH. Such other gases include inert gases, oxygen, nitrogen and others.

The standard procedure for calculation of ionized calcium is preferably used as described above. Thus, the millivoltage from the calcium electrode is displayed on a digital pH/mV meter such as the Orion Ionalyzer Model 801. This value for the sample and 3 calcium standards permits one to plot millivoltage vs. logarithm ionized calcium of the standards and extrapolate to the ionized calcium of the sample. This can be done manually or quickly on a small computer such as the Olivetti Programmer 101 or a Wang calculator or the like. This requires someone to punch in the value of the millivoltage from the standards and the sample. The millivoltage could be read from the digital pH/mV meter or a printer connected to it could directly print it out. For example, when the auto-analyzer is used, one could print out at the end of each circulation of thirty samples the sample number, the pH and the calcium electrode millivoltage such as 1, 7.30, 15 – 2, 7.45, 22, etc. Such a strip of thirty samples with 3 parameters each would be produced for each complete circuit of thirty measurements. In the cases where extrapolation is used, 2 such sets of 30 measurements having 3 parameters each could be produced since there will be one pH measurement for each of the 2 carbon dioxide partial pressures used. A technician could then punch the values into a calculator or a computer to get extrapolation to the ionized calcium at the original fresh pH for each sample. Alternatively, a large conventional computer can be used as known in the art to store all of the information and simply print out the sample number, pH and ionized calcium at the end of the test procedure.

Although it is preferred when using the extrapolation methods of this invention to obtain 2 arbitrary points, in some cases, the test serum used which will have changed from its original pH can be tested to obtain its ionized calcium concentration and pH by the use of the calcium electrode and pH electrode respectively and these values obtained can be used to plot for example point A in FIG. 6 and point F in FIG. 7. This is valid when such a pH already present in the serum is within the pH range 7.10 to 7.75 and yet not so close to the other pH produced by equilibration with an arbitrary $CO_2$ that an accurate straight line cannot be produced (FIG. 6 or FIG. 7). However, it is preferred to select the 2 arbitrary values by equilibration with arbitrary partial pressures of carbon dioxide as previously described.

It should further be understood that flow rates of gases in the systems noted can be varied greatly as desired. For example, in the autoanalyzer, flow rates of 100 ml per minute for approximately 7 to 9 minutes can be used for original equilibration. These rates can vary greatly. The flow rates only determine the time necessary for equilibration which time can vary depending upon equipment used.

In still another variation of this invention, where large numbers of samples are to be tested in screening procedures, it is possible to eliminate the original test to determine the original pH before the serum has changed from its in vivo pH. In this method, the procedures described above are carried out; however, one utilizes an arbitrary original pH which is preferably the average normal pH for human beings, i.e, 7.39. Thus, in any of the examples, instead of using Jones' serum's pH of 7.35, 7.39 is used and an indication of the original or in vivo ionized calcium concentration is obtained although in some cases such indication is not as accurate as that obtained by using the measured original pH of Jones' serum.

The semi-log plot of $Ca^{++}$ vs. pH in the specified pH range as illustrated in FIG. 6, produces a straight line for any serum sample, regardless of total $Ca^{++}$, total protein and other natural factors present. The slope of the straight line is different for different samples. Thus, no mathematical correction (as for average serum) can be applied if a measurement as precise as the electrode is capable of measuring is desired, since the average slope would, if applied to several different sera to extrapolate a pH correction, produce an error in excess of existing electrode precision. The method of this invention can produce a custom-made specific and unique slope for each serum and can be used to correct for ph in that serum sample alone. However, where a measurement as precise as the electrode is capable of measuring is not necessary as in a screening test, acceptable accuracy can be obtained by use of a straight line slope from pooled normal sera as will be described.

The discovery that the plot of the logarithm of ionized calcium versus the pH of a serum sample on semi-log paper, at least in the pH range of 7.1 to 7.75 produces a straight line for any serum sample, regardless of total calcium, protein and other natural factors present, is highly useful in determining original ionized calcium in a body fluid to be tested. For example, in a screening test, ionized calcium concentration of a serum sample can be plotted at two or more pH values and the points obtained used to draw a straight line on semi-log paper. The ionized calcium concentration of that serum sample at an average normal pH of for example 7.39 can then be read directly from the line drawn.

In still another method of using the straight line discovery, pooled serum from a group of normal people without known diseases can be tested and a graph drawn on which is plotted the log ionized calcium concentration versus pH at a number of points. This line can be said to define an average normal slope. One can then assign an arbitrary normal pH of 7.39 to the serum being tested. The slope obtained as the average normal, can then be drawn through a point plotted on semi-log paper of log calcium ionized concentration versus pH of a specific sample being tested and at any pH at which that sample is between 7.1 and 7.75, and the calcium ionized concentration at the average normal pH of 7.39 can be directly read. This is highly useful as a rough screening test which in many cases gives accurate results.

Of course in actual practice in a clinical laboratory, the average normal slope of average normal serum, once determined can be used in the slope methods without repeating the measurement steps to obtain such slope in connection with each serum sample tested. The average normal sloe for human serum, as measured on pooled serum or an average of slopes obtained by measuring a large number of individual serum samples of normal persons is about 0.30. Thus, for a rough screening test of the types noted herein one need only make a single measurement of pH and ionized calcium in the range pH 7.1 to 7.75, plot the point obtained on semi-log paper and apply the average normal slope line as described.

In a particularly useful screening method for determining ionized calcium concentration of a serum sample taken from the body to obtain the ionized calcium concentration of that serum in the body, the sample is first equilibrated with a carbon dioxide concentration which is known to bring most sera near to an average normal pH of 7.39. For example, $CO_2$ partial pressures of from 4 to 6% and preferably 5% (40 mmHg) is used. The ionized calcium concentration of the sample and the pH of the sample produced is then measured and located on semi-log paper graphing concentration of ionized calcium against pH as in FIG. 6. The normal slope for log ionized calcium vs. pH for average normal serum (average normal pooled serum) is then used to form a line on the graph running through the point plotted. One can then read the approximate ionized calcium concentration of that serum sample at an average normal pH of 7.39. The method of equilibrating with $CO_2$ is preferred to merely measuring the ionized calcium concentration vs. pH and plotting on a graph as in the preceding paragraph since the pH produced by first equilibrating will bring the serum sample closer to the average normal pH of 7.39 and thus there will be less chance of error since the average normal slope pH correction will often be less than that required when utilizing the method of the preceding paragraph. Of course, all pH and calcium ion concentration measurements can be made as in Examples 1–4 using the apparatus previously described.

It should further be understood that the specific slope of a particular serum can be measured merely by varying the pH of that serum by addition of carbon dioxide, and plotting the various ionized calcium concentrations at the varying pHs. Such slope can itself have diagnostic uses by comparing such slope with the slope for average normal pooled serum when so plotted.

It should be understood that this application refers to a straight line relationship by plotting body serum samples as a function of pH vs. ionized calcium concentration on semi-log paper. Any type of graph paper which results in a straight line relationship is sufficient, and should be considered the full equivalent of the semi-log graph paper described. For example, anti-log paper can be used.

A method of determining total original calcium concentration in a serum sample when that serum sample was withdrawn from the body can be carried out by using the methods of this invention to determine original ionized calcium concentration of that sample when withdrawn from the body, and a second step wherein the ionized calcium concentration is changed and determined at the original pH or an estimated average normal pH to obtain the total calcium concentration originally. The change is carried out by the use of a calcium ion addition to the serum sample. It is found that the following ratio exists:

$$\frac{Io}{To} = \frac{If}{Tf} \qquad (eq. 1)$$

where,
Io is the ionized calcium concentration of the original serum sample at a known pH or estimated average normal pH (mg%),
If is the ionized calcium concentration after the addition of the calcium ions at that known pH or average normal estimated pH (mg%),
To is the total calcium concentration originally in the serum sample (mg%),
Tf is the total calcium concentration finally after addition of calcium ions (mg%).

In finding total original calcium, the following working formula derived from the first equation is used:

$$To = \frac{IoVaTa}{If(Vo + Va) - IoVo} \qquad (eq.\ 2)$$

where,
Io, If, To are defined as described above,
Va is the volume of the liquid form of the calcium ions added (ml),
Ta is the total concentration of calcium ions in the solution (mg%),
Vo is the volume of the original sample (ml).

Where powdered calcium ions are added, this formula is equal to the equivalent formula as follows:

$$To = \frac{Io \times \text{amount calcium added in mg}}{IfVo - IoVo} \qquad (eq.\ 3)$$

Equation 2 is derived from the known relationship of equation 1 by rearranging equation 1 as follows:

$$To = (Io \times Tf)/If$$

Since $$Vo\ To + Va\ Ta = Vf\ Tf,\ \text{or}\ Tf = \frac{Vo\ To + Va\ Ta}{Vf + Va}$$

we can substitute to obtain the equation $$To = \frac{Io}{If} \times \left(\frac{Vo\ To + Va\ Ta}{Vo + Va}\right)$$

which in turn rearranges to the working formula of equation 2.

In using this formula it is clear that the only unknown and the value for which it is necessary to solve is To. All values of the right side of the equation are known (Va, Ta, Vo) or measurable with a calcium electrode (Io, If).

As is known, methods for measuring total calcium concentration usually involve atomic absorption, photometry and use entirely different techniques from the technique of this invention.

In an example of finding total original calcium concentration of a serum sample, the volume of the serum sample (Vo) is measured. The ionized calcium concentration of the serum sample is measured using a calcium electrode and any of the preceding methods of determining original ionized calcium concentration (Io) of that sample in the human body from which it was taken. A small known volume (Va) of $CaCl_2$ aqueous solution of known calcium concentration (Ta) is then added to form a resultant solution of known volume (Vf) and the final ionized calcium concentration (If) is then measured using any of the methods of this invention previously described. Both original ionized calcium concentration and final ionized calcium concentration of the resultant solution are determined at the same pH which is preferably the original pH of the serum used when withdrawn from the body although it can be an arbitrary pH as for example 7.39. The numbers are simply plugged into equation 2 and the calculation of original total calcium made.

Figure 9:
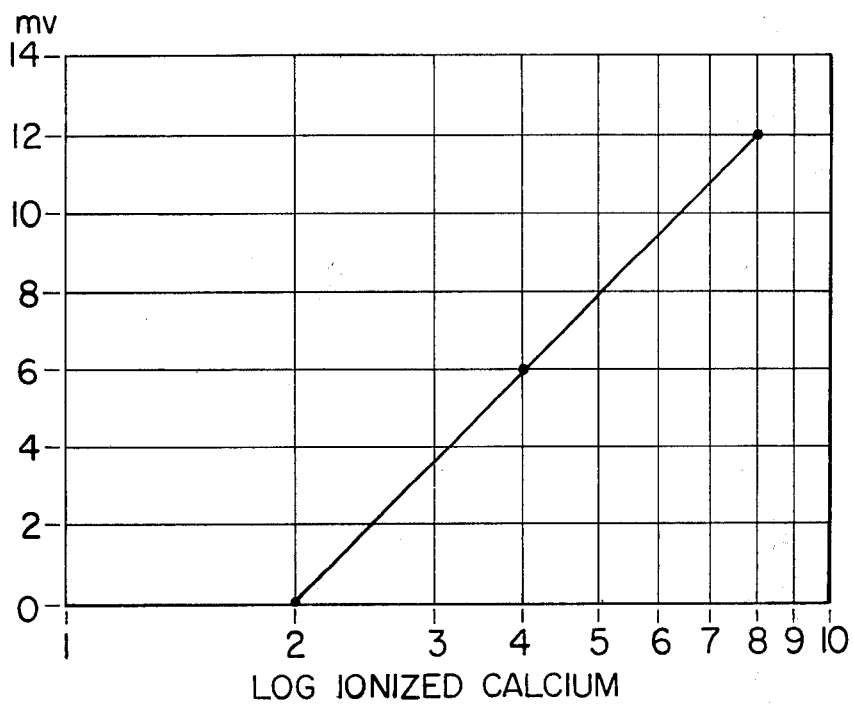
FIGS. 9–13 are illustrative graphs illustrating procedures of this invention.

Turning now to an improved method for obtaining calibration curves on known calcium electrodes such as the Orion electrode and methods of forming ionized calcium serum standards for use in such calibration are now described. All known calcium electrodes to date obtain calibration curves by the use of aqueous ionized calcium solution standards which are water or other solutions which do not contain protein or other natural ingredients contained in blood but which contain only those inorganic constituents which one chooses to mix into a water base. The reasons for using aqueous ionized calcium standards has been twofold. Since ionized calcium in blood is pH dependent, there has not been until the development of this invention any practical way to cope with such pH dependence in standards. In addition, one can prepare an aqueous solution in which all the calcium is theoretically ionized such that one can assume that the ionized calcium concentration is equal to the total calcium concentration which can be measured and calculated by many conventional techniques. Such aqueous standards are generally used by using solutions of calcium concentration of say 2, 4 and 8 mg% and measuring the mV readouts with the calcium electrode and plotting the mV vs. log of the ionized calcium as shown in FIG. 9. One then measures the mV readout of the blood sample with the calcium electrode and reads this mV horizontally to intercept the calibration line and then down to the corresponding ionized calcium value.

Using such an aqueous calibration curve to measure blood or serum samples is based on the assumption that if one measured serum samples with the same ionized calcium concentration as the aqueous standards one would obtain the identical calibration curve. This assumption is not always true and there is sometimes in effect a phase shift in going from aqueous to serum samples. Some evidence to indicate that the assumption is not always correct is that using the described Orion electrode on different days, with good aqueous calibration slopes, yields very different values on serum from similar people strongly suggesting a phase shift and certainly suggesting that better calibration standards would be desirable.

It has now been found that more consistent precise results are obtained in calibration and ionized calcium concentration testing of serum if one calibrates the calcium electrodes with known serum standards of ionized calcium concentration having the ionized calcium in body serum rather than aqueous solutions. It is pointed out here that the methods of this invention will work when the calcium electrodes are calibrated with aqueous ionized calcium standards although more reliable and consistent results are obtained when using calibration standards of known calcium ion concentration in blood serum which could be otherwise termed "serum ionized calcium standards".

To obtain serum standards for use in calibration, the ratio discussed above:

$$\frac{Io}{To} = \frac{If}{Tf}$$

is used. For example, pooled normal human serum, or a lyophilized serum prepared from pooled normal human serum, with a total calcium concentration of about the normal value of 9.6 mg% as measured by conventional total calcium measuring methods is assigned a value of normal of 4.4 mg% ionized calcium. Preferably the pooled human serum used is obtained from a large number of say 100 average health humans. The pH of the pooled serum is brought to an average normal pH of 7.39 as by addition of $CO_2$ gas. A small volume of highly concentrated calcium ion containing solution such as $CaCl_2$ aqueous solution, having a calcium ion concentration greater than 4.4 mg%, is added to a sample of the normal human serum. The total calcium concentration of the mixture can then be measured by conventional means. Alternatively, the total calcium concentration can be increased even higher by adding more of the $CaCl_2$ solution and re-lyophilizing the mixture. Additional higher standards can be made by repeating the prior step. Any arbitrary value of calcium ion concentration can be assigned to the normal pooled serum although a value between 4.0 to 4.8 mg% and preferably 4.4 mg% is preferably used since this is believed to be the true absolute normal value.

For example, if the added calcium chloride brings the sample to a measured total calcium value of 14.4 mg%, these values can be plugged into the above equation (1) indicating that the newly made serum standard has 6.6 mg% ionized calcium concentration at a pH of 7.39. Similarly, when the newly made serum standard has a total calcium of 19.2 mg%, the ionized calcium concentration is 8.8 mg%. Of course all values are determined at comparable pHs such as at pH 7.39 using the methods of this invention to correct for any pH variance in the actual sample.

These serum standards can be used for calibration of calcium electrodes such as the Orion electrode and will yield more consistent accurate results than when calibration is carried out by use of aqueous standards.

Another example of preparing and using the ionized calcium serum standards of this invention is as follows: one arbitrarily assigns a value for ionized calcium to a mixed pool of serum obtained from normal people at a pH of 7.39, or for convenience 7.30, to act as an anchor point. The arbitrarily assigned value is 4.4 mg% since all prior evidence seems to indicate that this is the average normal ionized calcium concentration of serum in the body. Next, one prepares two or more higher ionized calcium serum standards from a portion of the pooled serum standard base.

If two additional standards are prepared, the three stadards are then brought to a pH of 7.40 by $CO_2$ equilibration. The three standards are then placed in the calcium electrode and the ionized calcium mV of them obtained and plotted on the calibration curve as in FIG. 10 on semi-log paper of log ionized calcium vs. mV.

In the next step, the ionized calcium of each standard is measured as a function of pH. This is done by varying the pH of each serum standard with $CO_2$ by equilibration and measuring the mV obtained by the calcium electrode at the various pHs and reading these mVs horizontally on the serum calibration curve derived in FIG. 10 and then down to the corresponding ionized calcium. The straight line log ionized calcium vs. pH relationship described in FIG. 6 is obtained and shown again in FIG. 11 for each standard.

Figure 11:
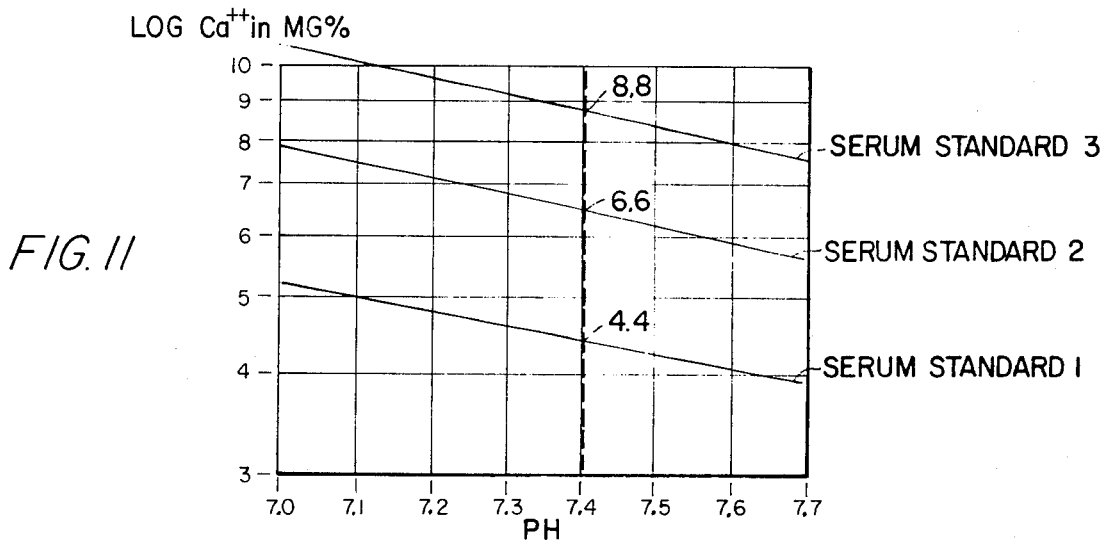

In a next step, the ionized calcium of each serum standard defined as a function of pH of these standards, may be used at any pH, so long as it is within a range of pH which is 7.10 to pH 7.75, to derive a daily serum calibration curve. If a standard should fall outside the defined pH range of 7.1 to 7.75, it could then be mixed with 5% $CO_2$ which would in most cases bring it within the defined range. On a given day, using the serum standards of FIG. 11 as an example:

a. Serum standard 1 might be measured at a pH of 7.20 and give a reading of 1.0 mV. FIG. 11 shows that this standard at a pH of 7.20 has an ionized calcium of 4.75 mg%.

b. Serum standard 2 might be measured at a pH of 7.60 and give a reading of 3.5 mV. FIG. 11 shows that this standard at a pH of 7.60 has an ionized calcium of 6.0 mg%.

c. Serum standard 3 might be measured at a pH of 7.50 and give a reading of 7.2 mV. FIG. 11 shows that this standard at a pH of 7.50 has an ionized calcium of 8.4 mg%.

One then plots the mV of the calcium electrode vs. the log ionized calcium for the pairs of values:

| mV | Ca++ |
|---|---|
| 1.0 | 4.75 |
| 3.5 | 6.0 |
| 7.2 | 8.4 |

Figure 10:
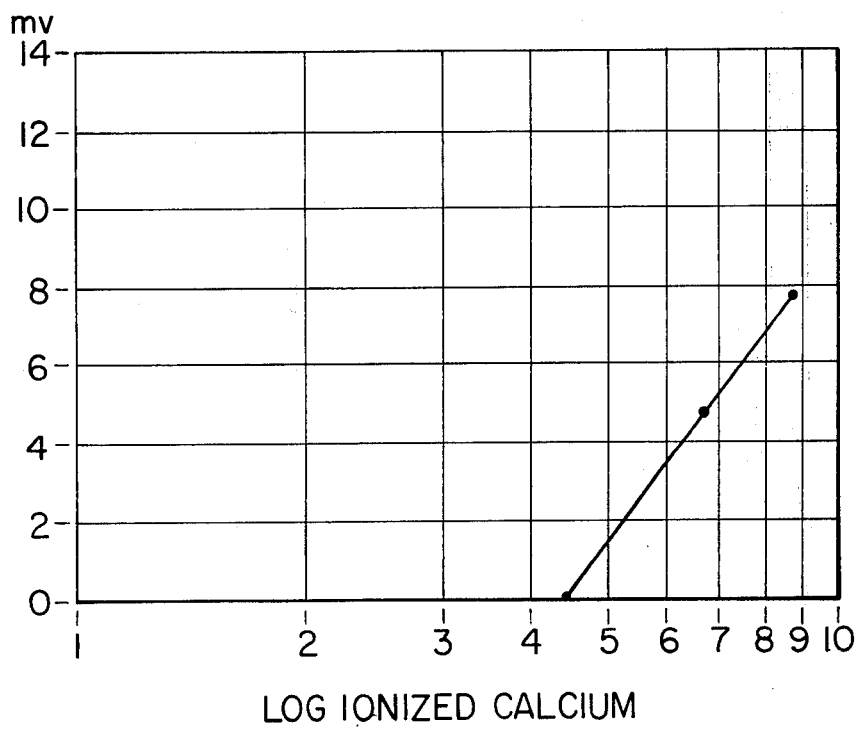
Figure 12:
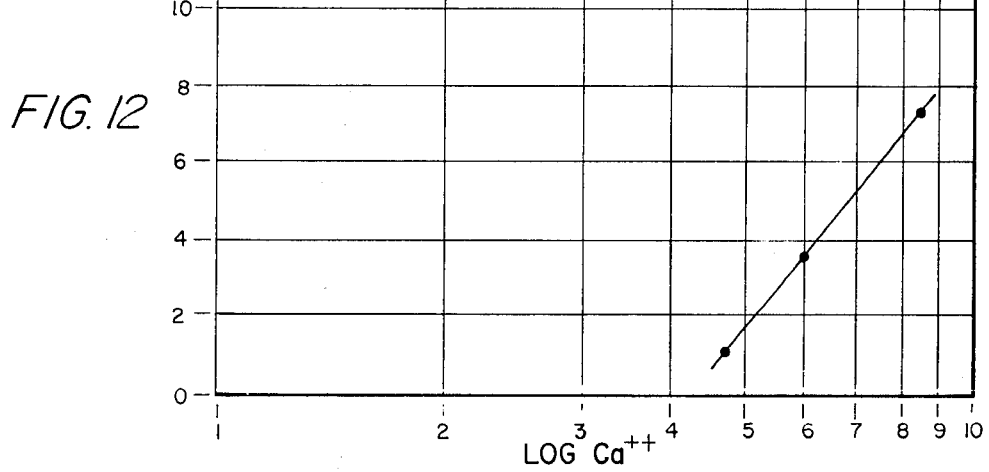

These values would plot out as in FIG. 12 which, because of the arbitrary selection of values here for the purposes of clear illustration, yields the same slope as in FIG. 10.

An alternative to the last-mentioned step which is a particularly convenient alternative to the use of two or three serum standards to obtain a calibration curve, is to use only a single serum standard at various pHs. Thus, the pooled single serum standard from normal average humans is used. One produces various pHs in this single standard by using different $CO_2$ gas mixtures to equilibrate to different pH values. One can also use a single $CO_2$ gas mixture to produce varying degrees of saturation (partial saturation) and a corresponding range of pH values. For example, a 10% $CO_2$ mixture can be used to rapidly produce a gradient of pH values between 7.1 and 7.75. One measures the mV of ionized calcium at various pHs in this range which would approximately read as shown in FIG. 11 the ionized calcium present in the single serum sample at each pH. Then one plots the mV against the corresponding log ionized calcium to obtain the calibration curve as in FIG. 12. In this method one takes advantage of the fact that ionized calcium changes with pH and that by changing the pH of a single serum standard aliquot one produces several different ionized calcium serum standards all in one sample cup without the need to use 2 or 3 different samples from different sera standards.

Calcium electrode repeatability can be verified before beginning to measure serum samples by taking advantage of the straight line log ionized calcium vs. pH relationship of this invention in a single sample. The straight line relationship on semi-log paper of log ionized calcium vs. pH can of course be expressed alternatively as a plot on regular linear graph paper of mV from calcium electrode vs. pH. Thus, the pH of any serum sample can be varied with $CO_2$ and the pH as measured with a pH electrode, and millivolt readings from a calcium electrode can be measured simultaneously either at discrete intervals as with flow through electrodes or continuously as with dip electrodes. The ionized calcium mV is then plotted on linear paper against the corresponding pH. If a good straight line is produced by the points plotted, this verifies repeatability of the calcium electrode which can then be reliably used on unknown serum or blood samples in patients.

Figure 13:
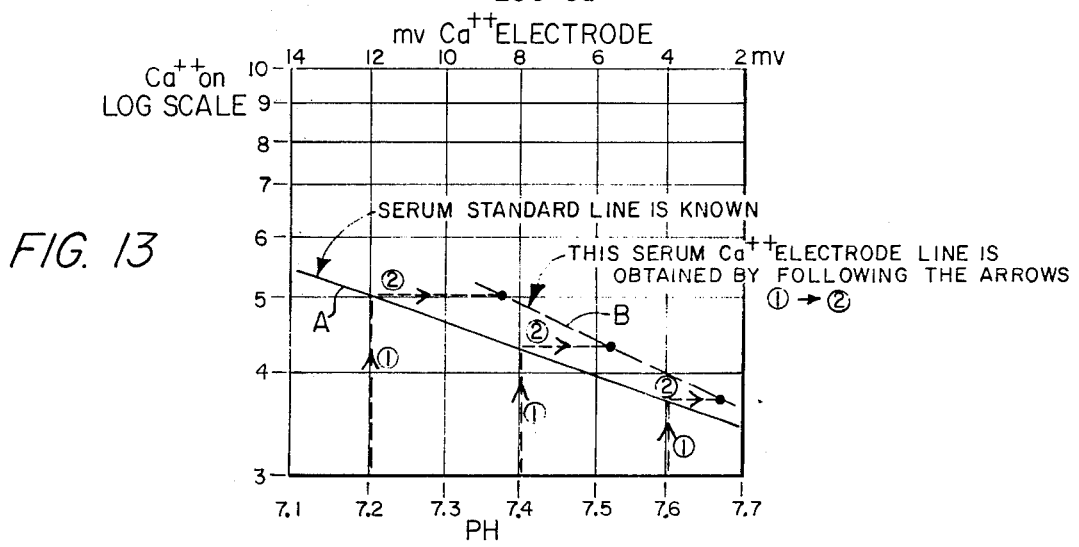

Another method of verifying the calcium electrode repeatability while simultaneously obtaining the calcium electrode serum calibration line can be carried out on a serum standard whose relationship to pH has been previously defined as in FIG. 11. As demonstrated in FIG. 13, the vertical scale and bottom horizontal scale are used to plot log ionized calcium vs. pH for that same serum standard. A top horizontal scale in millivolts is provided. Thus, the bottommost line is a known line and can be drawn in on the graph paper as in FIG. 13 before starting or this information can be stored in a calculator or computer. Carbon dioxide is then used to vary the pH of the serum standard. The various 2 or more pHs produced as measured by a pH electrode and the mV from the calcium electrode corresponding to each pH, are recorded. For each pH point at which an ionized calcium mV reading is obtained, one reads up vertically from that pH until one intersects the serum standard line A previously drawn. Then from this intersection one reads horizontally over until one reaches the mV reading on the top horizontal scale, plotting a point (X) there. This is done for 3 different pH-calcium millivolt pairs in FIG. 13 to yield line B. The straightness of the line B is a measure of repeatability of the calcium electrode and the slope of line B represents the calcium electrode calibration line as in FIG. 12.

In any body fluid in which the ionized calcium bears a quantitative relationship to pH as described for blood serum, then this fluid can be used in ionized calcium determinations as described herein and should be considered the full equivalent of "serum" as used in this application. Thus, the term "serum" is meant to include lyophilized serum, serum obtained directly from the body and other body fluids.

While ionized calcium and total calcium have been used as examples throughout the specification, this invention is applicable to determinations of other divalent cations in body fluids which other divalent cations are pH dependent as described with relation to calcium. Thus, all the methods and apparatus of this invention can be used for determinations of ionized magnesium and total magnesium in serum in the same manner and under the same conditions as described herein for use with calcium.

What is claimed is:

1. A method of determining approximate original ionized calcium concentration in serum taken from the body, said method comprising adjusting the pH of said serum to a specific predetermined average normal pH and then measuring the ionized calcium concentration of said serum.

2. A method in accordance with the method of claim 1 wherein $CO_2$ gas addition is used in said pH adjusting.

3. A method of determining original ionized calcium concentration in serum taken from the body, said method comprising, testing to determine the original pH of the serum when it is removed from the body, permitting said original pH to change, and later determining the ionized calcium concentration at said original pH.

4. A method in accordance with the method of claim 3 wherein said later determining is carried out by equilibrating said serum with a first known $CO_2$-gas mixture to obtain a first arbitrary pH value, equilibrating said serum with a second $CO_2$-gas mixture to obtain a second arbitrary pH value, plotting the logarithm of each $CO_2$ partial pressure against the pH it produced on semi-log paper to produce first and second points, connecting the two points by a straight line an extrapolating from the known original pH to determine the $CO_2$ partial pressure required to produce the original pH, producing the original pH in the sample and directly measuring the ionized calcium concentration at said original pH.

5. A method in accordance with the method of claim 3 wherein said later determining is carried out by adjusting the pH of said serum to said original pH by adjustment of said serum with a $CO_2$-gas mixture and then measuring the ionized calcium concentration.

6. A method in accordance with the method of claim 5 wherein said $CO_2$-gas mixture is flowed to said serum while simultaneously monitoring the pH of said serum to reach said original pH.

7. A method in accordance with the method of claim 5 wherein a plurality of different serum samples are selected, and said later determining is carried out by adjusting simultaneously the pH of all of the samples to an arbitrary pH near the normal human pH range, and sequentially adjusting the pH of each serum sample to its original pH by equilibration of each said serum sample with a $CO_2$-gas mixture after which ionized calcium concentration is directly measured.

8. A method in accordance with the method of claim 3 wherein said later determining is carried out by equilibrating with a first $CO_2$-gas mixture and obtaining a first ionized calcium concentration at a first pH value of said serum, then equilibrating with a second $CO_2$-gas mixture and obtaining a second ionized calcium concentration at a second pH value of said serum, plotting the points of said first and second obtained ionized calcium concentrations on a semi-log graph with log calcium concentration against pH and drawing a straight line therebetween to cause the original ionized calcium concentration to appear on said line at the original pH value.

9. A method in accordance with the method of claim 8 wherein said first and second pH values lie within the range of from pH 7.10 to 7.75.

10. A method in accordance with the method of claim 8 wherein said method is carried out on a plurality of samples and after said first testing to determine the original pH, each of said plurality of samples is simultaneously equilibrated with said first gas mixture and each of said samples is simultaneously equilibrated with said second $CO_2$-gas mixture.

11. A method of determining approximate original ionized calcium concentration in a serum sample taken from the body, said method comprising allowing the pH of said serum sample to change from its pH in the body, and determining the ionized calcium concentration of said sample at a specific predetermined average normal pH.

12. A method of determining approximate original ionized calcium concentration in serum taken from the body, said method comprising, measuring the ionized calcium concentration of said serum at a pH other than a specific predetermined average normal body serum pH, and determining from the measurement obtained the approximate original ionized calcium concentration of said serum at said specific predetermined average normal body serum pH.

13. A method of verifying ionized calcium electrode repeatability and precision prior to using said electrode to determine ionized calcium concentration of serum samples, said method comprising, adjusting the pH of a serum sample with $CO_2$ gas and making measurements of pH and corresponding calcium electrode millivolts at three pH values in the range of pH 7.1 to 7.75, plotting the pH values measured against corresponding calcium millivolt values measured at three points, and fitting a straight line through said three points with the straightness of said line being an indication of repeatability and precision.

14. A method of determining approximate original ionized calcium concentration in serum taken from the body, said method comprising, equilibrating said serum sample with a first $CO_2$ gas mixture and obtaining a first ionized calcium concentration at a first pH value of said serum, then equilibrating with a second $CO_2$ gas mixture and obtaining a second ionized calcium concentration at a second pH value of said serum, plotting the points of said first and second obtained ionized calcium concentrations on a semi-log graph with log calcium concentration against pH and drawing a straight line therebetween, and selecting a specific predetermined average normal pH value on said line and obtaining an approximation of said original ionized calcium concentration.

15. A method of determining approximate original ionized calcium concentration in serum taken from the body, said method comprising, equilibrating said serum sample with a first known $CO_2$ gas mixture to obtain a first arbitrary pH value, equilibrating said serum with a second $CO_2$ gas mixture to obtain a second arbitrary pH value, plotting the logarithm of each $CO_2$ partial pressure against the pH it produced on semi-log paper to produce first and second points, connecting the two points by a straight line and extrapolating from a specific predetermined average normal pH to determine the $CO_2$ partial pressure required to produce an average normal pH, then using said specific $CO_2$ partial pressure required to produce the specific predetermined average normal pH in the sample and directly measuring the ionized calcium concentration at said specific predetermined average normal pH.

16. A method of obtaining approximate original ionized calcium concentration in serum taken from the body, said method comprising,
  measuring the pH value and corresponding ionized calcium concentration value of a sample of said serum at a pH in the range of pH 7.1 to 7.75,
  plotting said value as a point on a semi-log graph of pH vs. log ionized calcium,
  producing a straight line through said point with said line having a slope corresponding to the average normal slope of ionized calcium concentration for body serum from average normal persons,
  and determining said approximate original ionized calcium concentration of said serum sample by reading from said graph at a predetermined pH value.

17. A method in accordance with the method of claim 16 wherein said predetermined pH value is a specific predetermined average normal pH.

18. A method in accordance with the method of claim 16 wherein said predetermined pH value is the original pH of said serum sample when taken from said body.

19. A method in accordance with the method of claim 16 wherein said serum sample is adjusted in pH to a value in the range from pH 7.1 to 7.75 with the use of $CO_2$ gas prior to said measuring.

20. A method of determining original total calcium concentration in serum taken from the body after first determining ionized calcium concentration of said serum,
  said method comprising determining the volume ($Vo$) of a sample of said serum,
  determining the original ionized calcium concentration ($Io$) of said serum sample at a known pH,
  adding a known volume ($Va$) and known concentration ($Ta$) of calcium ions to said serum sample,
  again determining the ionized calcium concentration ($If$) of said serum at said known pH,
  and using the formula:

$$To = \frac{IoVaTa}{If(Vo+Va) - IoVo}$$

solving for said total original calcium concentration of said sample.

21. A method in accordance with the method of claim 20 wherein said known pH is the actual original pH of said serum sample when taken from the body and said original ionized calcium concentration is the actual original ionized calcium concentration of said serum sample when it was in the body.

22. A method in accordance with the method of claim 20 wherein said known pH is a specific predetermined average normal pH of body serum of normal persons and said original ionized calcium concentration is the approximate original ionized calcium concentration of said serum sample when it was in the body.

23. A method of simultaneously verifying calcium electrode repeatability and obtaining a calcium electrode serum calibration line by measurements on a single serum standard whose pH vs. ionized calcium relationship is known, said method comprising,
  forming a graph of log ionized calcium concentration on a vertical scale vs. pH on a bottom horizontal scale for said serum standard to produce a line A on said graph,
  adjusting the pH of said serum standard with $CO_2$ gas and making pH and corresponding calcium electrode millivolts measurements at three different pH values.
  establishing a top horizontal millivoltage scale on said graph,
  and for each pH value at which a calcium millivolt reading is obtained plotting a point on said graph which point is determined by reading vertically up from said pH value on the bottom horizontal scale to the intersection with line A and then horizontally across to the corresponding calcium electrode millivolt value on the top horizontal millivolt scale to thereby obtain three points on said graph,
  and fitting a straight line B through said three points with the straightness of the line B being an indication of the repeatability and precision of the calcium electrode and the slope of line B, as expressed millivolts calcium electrode vs. log ionized calcium being the calcium electrode calibration line.

24. A method of calibrating a calcium electrode using a pH electrode and a standard comprising a mixture of body serum and calcium ions whose concentration as a function of pH has been defined, said method comprising,
  obtaining an electrical readout from said pH electrode when testing said standard, which pH value specifies the ionized calcium concentration present,
  and recording an electrical readout from said calcium electrode at said known concentration.

25. A method in accordance with the method of claim 24 wherein a plurality of serum standards of different known calcium ion concentrations are used and the electrical readout of each serum standard is recorded in semi-log plot of mV ionized calcium vs. log ionized calcium concentration.

26. A method of producing a serum calcium standard of known ionized calcium concentration,
  said method comprising,
  selecting a normal serum sample with an ionized calcium concentration ($Io$) assigned an arbitrary value in the range of from about 4.0 to about 4.8 in mg% at a known pH value and a normal total calcium ($To$),
  measuring said total calcium concentration,
  adding calcium ions to said serum to change said ionized calcium concentration to a value ($If$) at said known pH and thus changing said total calcium ($Tf$),
  measuring said total calcium ($Tf$) after addition and determining said ionized calcium concentration $If$ at said known pH by solving the following equation where only $If$ is unknown:

$$\frac{Io}{To} = \frac{If}{Tf}.$$

27. A method in accordance with the method of claim 26 wherein said known pH value is a specific predetermined average normal serum pH value.

28. A method in accordance with the method of claim 26 wherein said normal serum is pooled serum from a large number of average healthy individuals.

29. In a method of accurately determining ionized serum calcium concentration of body serum the improvement comprising, utilizing a body serum sample containing an artificially added quantity of total calcium with at least some of said total calcium being in the form of ionized calcium as a serum standard in determining said concentration.

30. A testing apparatus for determining original ionized calcium concentration of serum taken from the body, said apparatus comprising a rotatable turntable, a plurality of serum sample containers mounted on said turntable and having upwardly facing container mouths, a cover positioned over said turntable to close said container mouths while permitting rotational movement with respect to said cover of said turntable along with said containers, means for rotating said turntable with respect to said cover at predetermined intervals to advance each of said containers to successive stations, means in said cover for passing a gas to a plurality of said containers at predetermined stations whereby the pH of said last-mentioned plurality of serum samples is simultaneously adjusted, a sampling tube mounted at one of said stations for withdrawing serum from a container at said one station.

31. A testing apparatus in accordance with claim 30 wherein said means in said cover for passing a gas is interconnected with a means for blending $CO_2$ gas with a second gas to form a $CO_2$-gas mixture.

32. A testing apparatus in accordance with claim 30 and further comprising said one station further mounting a pH electrode with said sampling tube and pH electrode being mounted for reciprocal movement toward and away from successive sample containers presented at said one station.

33. A testing apparatus in accordance with claim 32 wherein said means for passing a gas comprises a circular conduit having outlets for passing said gas simultaneously to all of said plurality of sample containers.

34. A testing apparatus in accordance with claim 32 wherein said sampling tube means is interconnected with a calcium electrode means for determining ionized calcium concentration of samples carried by said sample containers.

35. A testing apparatus in accordance with claim 32 wherein said one station further mounts an independent gas input means independent of said first-mentioned means for passing a gas.

36. A testing apparatus in accordance with claim 35 and further comprising a second of said stations adjacent to said one station comprising a final gas adjustment station and mounting a pH electrode and an independent gas input means.

37. In a testing apparatus for determining pH dependent values of a body fluid, which apparatus comprises a rotatable turntable with a plurality of serum sample containers mounted on the turntable and having upwardly facing container mouths lying substantially in a plane, the improvement comprising, a cover positioned over said container mouths to close said container mouths while permitting rotational movement of said turntable along with said containers with respect to said cover, said cover carrying gas conduit means having plural gas outlet means for passing a gas simultaneously to a plurality of said sample containers.

38. In a testing apparatus for determining pH dependent values of a body fluid, which apparatus comprises a plurality of sample containers having upwardly facing container mouths, the improvement comprising, a cover positioned over said container mouths to close said container mouths and maintain a predetermined gas atmosphere in said containers, said cover carrying gas conduit means having a plurality of gas outlet means for passing a gas simultaneously to a plurality of said sample containers.

39. A testing apparatus for determining pH dependent values of a body fluid, which apparatus comprises, a cover, a plurality of sample containers positioned below said cover and having upwardly facing container mouths mounted for sliding movement with respect to said cover, gas conduit means for passing a gas into said sample containers to actively mix said gas with liquid contents carried by said containers, and means for allowing escape of gas whereby gas flow from said gas conduit means and concurrent mixing are allowed.

40. A testing apparatus in accordance with claim 39 wherein said gas conduit means is positioned to pass said gas to said liquid contents above the surface of said liquid to create a swirling action in said liquid and enable rapid mixing of said gas and liquid.

* * * * *